US010562027B2

(12) United States Patent
Hsiung et al.

(10) Patent No.: US 10,562,027 B2
(45) Date of Patent: Feb. 18, 2020

(54) SYSTEM AND METHOD FOR DETECTION IN ION FLUID

(71) Applicant: Winnoz Technology, Inc., Taipei (TW)

(72) Inventors: Le-Chang Hsiung, Taipei (TW); Chun-Yen Tai, Taipei (TW); Yu-Lin Chen, Taipei (TW); Fang-Yu Lin, Taipei (TW); Chuan Whatt Eric Ou, Singapore (SG)

(73) Assignee: Winnoz Technology, Inc., Taipei (TW)

( * ) Notice: Subject to any disclaimer, the term of this patent is extended or adjusted under 35 U.S.C. 154(b) by 0 days.

(21) Appl. No.: 15/141,978

(22) Filed: Apr. 29, 2016

(65) Prior Publication Data

US 2016/0320332 A1 Nov. 3, 2016

Related U.S. Application Data

(60) Provisional application No. 62/155,150, filed on Apr. 30, 2015.

(51) Int. Cl.
*G01N 27/30* (2006.01)
*G01N 27/327* (2006.01)
(Continued)

(52) U.S. Cl.
CPC ...... *B01L 3/502753* (2013.01); *G01N 27/327* (2013.01); *G01N 27/4145* (2013.01); *G01N 33/54366* (2013.01); *G01N 33/6803* (2013.01); *G01N 33/721* (2013.01); *B01L 2200/10* (2013.01); *B01L 2300/06* (2013.01);
(Continued)

(58) Field of Classification Search
None
See application file for complete search history.

(56) References Cited

U.S. PATENT DOCUMENTS 5,200,051 A * 4/1993 Cozzette ............... B01L 3/0268
204/403.07
2004/0126814 A1 7/2004 Singh et al.
(Continued)

FOREIGN PATENT DOCUMENTS

| CN | 101051037 | 10/2007 |
|---|---|---|
| CN | 101256167 | 9/2008 |
| TW | 201441610 | 11/2014 |

OTHER PUBLICATIONS

Kissinger et al. (J. Chem. Ed. 60/9, 1983, pp. 702-706).*
(Continued)

*Primary Examiner* — Gurpreet Kaur
*Assistant Examiner* — Steven E Rosenwald
(74) *Attorney, Agent, or Firm* — Amin, Turocy & Watson, LLP (57) ABSTRACT

An electrochemical extended-gate transistor (EET) system is provided, the system includes: a field effect transistor (FET), having a gate, a source, and a drain; a potentiostat, having a working electrode, a counter electrode, and a reference electrode; wherein the working electrode is coupled with a detection region, and the counter electrode is coupled with the gate; wherein the detection region, the gate, and the reference electrode are arranged in an ion fluid; wherein the potentiostat is configured to generate redox in the ion fluid by an electrochemical method to detect the target. A method for detecting targets are used to such system.

17 Claims, 13 Drawing Sheets

(51) Int. Cl.
*G01N 27/414* (2006.01)
*B01L 3/00* (2006.01)
*G01N 33/543* (2006.01)
*G01N 33/68* (2006.01)
*G01N 33/72* (2006.01)
*C12Q 1/6806* (2018.01)

(52) U.S. Cl.
CPC . *B01L 2300/069* (2013.01); *B01L 2300/0636* (2013.01); *B01L 2300/0681* (2013.01); *B01L 2300/087* (2013.01); *B01L 2300/0883* (2013.01); *B01L 2400/043* (2013.01); *B01L 2400/0406* (2013.01); *B01L 2400/088* (2013.01); *C12Q 1/6806* (2013.01)

(56) References Cited

U.S. PATENT DOCUMENTS

| | | | | |
|---|---|---|---|---|
| 2006/0223170 | A1* | 10/2006 | Kamahori | G01N 27/4145 435/287.2 |
| 2007/0000778 | A1* | 1/2007 | Hsiung | G01N 27/4148 204/419 |
| 2007/0155037 | A1* | 7/2007 | Chou | G01N 27/414 438/49 |
| 2008/0009002 | A1 | 1/2008 | Gruner et al. | |
| 2013/0056353 | A1* | 3/2013 | Nemirovsky | G01N 27/4146 204/416 |

OTHER PUBLICATIONS

Bian et al. (Biomed Microdevices, 2011, 13:345-352).*
Ishige et al. (Biosensors and Bioelectronics, 24, 2009, 1096-1102).*
Park et al. (Sensors and Actuators B, 83, 2002, 90-97).*
Nakazato (2014 Chemistry integrated circuit: chemical system on a complementary metal oxide semiconductor integrated circuit. Phil. Trans. R. Soc. A 372: Jan. 9, 2013).*
Written Opinion and International Search Report for International Patent Application No. PCT/CN2016/080679 dated Jun. 28, 2016, 8 Pages.
Taiwanese Office Action for Taiwanese Patent Application No. 105113438 dated Nov. 9, 2017.

* cited by examiner

SYSTEM AND METHOD FOR DETECTION IN ION FLUID

BACKGROUND OF THE DISCLOSURE

1. Field of the Disclosure

The present disclosure relates to a field effect transistor (FET)-based biosensor, particularly a FET-based biosensor using electrochemical method to improve detection limit and sensitivity in a high-ion fluid.

2. Description of the Related Art

Figure 1A:
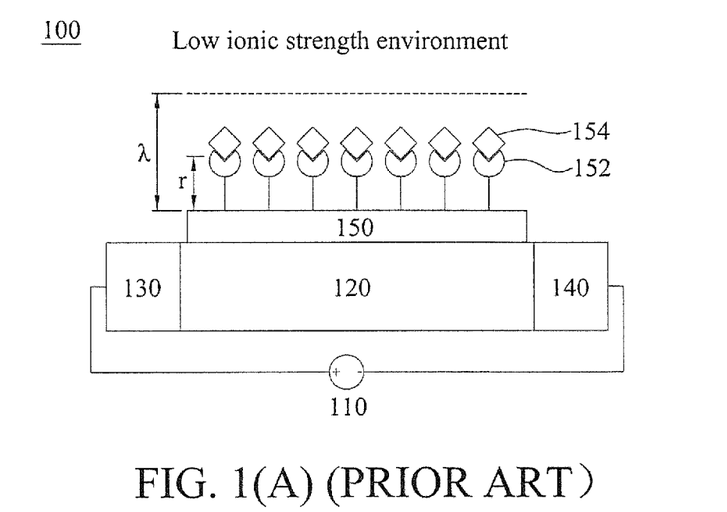
FIGS. 1(A) and 1(B) illustrate a conventional FET-based biosensor and the relationship between ionic strength and Debye length.

The determination of the presence of substances, such as proteins or some specific targets, in a blood or serum sample is important in diagnosis. For example, in an ordinary FET-based biosensor 100 as shown in FIG. 1 (A), the gate 150 is modified with antibodies or some recognition elements 152 for the detection of specific biomarkers 154. When the biomarkers 154 are caught by the recognition elements 152, the charges of the biomarkers 154 will accumulate on the gate surface to cause a potential on the gate 150, such that the biomarker concentration can be determined by the current flowing through the substrate 120 between the source 140 and the drain 130 (i.e., $I_{DS}$) in the presence of a voltage source 110.

However, if the test sample has a high ionic strength, the potential contributed by the charges of the biomarker will be neutralized by the ions in the sample. As such, once the distance (r) between the gate surface and the caught biomarker exceeds a specific length (FIG. 1(B)), i.e. Debye length ($\lambda$) over which the ions in the sample screen out electric potential of caught biomarkers. The electric potential screened out may reduce the current flowing through the substrate 120 between the source 140 and the drain 130, such that the system cannot provide desired detection limit and sensitivity to detect the concentration of biomarker.

Figure 2:
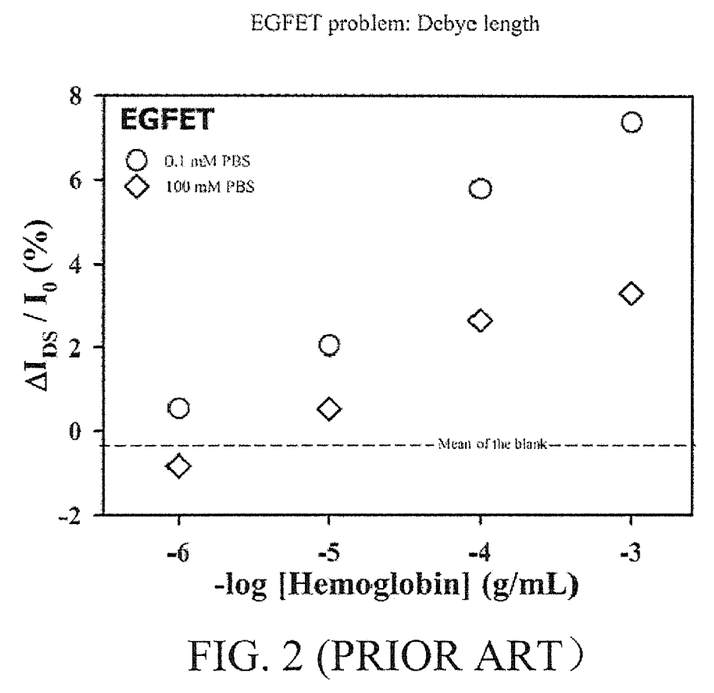
FIG. 2 shows results of using conventional EGFET system for detecting hemoglobin in 100 mM PBS and 0.1 mM PBS.

Therefore, the conventional FET biosensor is unable to provide desire detection limit and sensitivity to detect a target biomarker in a high-ion fluid (ionic strength is ~150 mM; Table 1). FIG. 2 further shows the comparison of detection results of conventional extended-gate field effect transistor (EGFET) in 100 mM phosphate buffer solution (PBS) (ionic strength is ~400 mM; Table 1) and in 0.1 mM PBS (ionic strength is ~0.4 mM; Table 1). As a result, the detection limit in high-ion fluid is lower than that in low-ion fluid, which can be attributed to the reduction of Debye length. Referring to Table 1, Debye length can be further decreased to ~0.48 nm in 100 mM PBS, which is smaller than the diameter of hemoglobin (~5 nm, Biol Proced Online 2009, 11: 32-51). Therefore, the charges carried by hemoglobin are insufficient to generate potential on the gate of EGFET to induce corresponding $I_{DS}$ for detection.

Figure 1B:
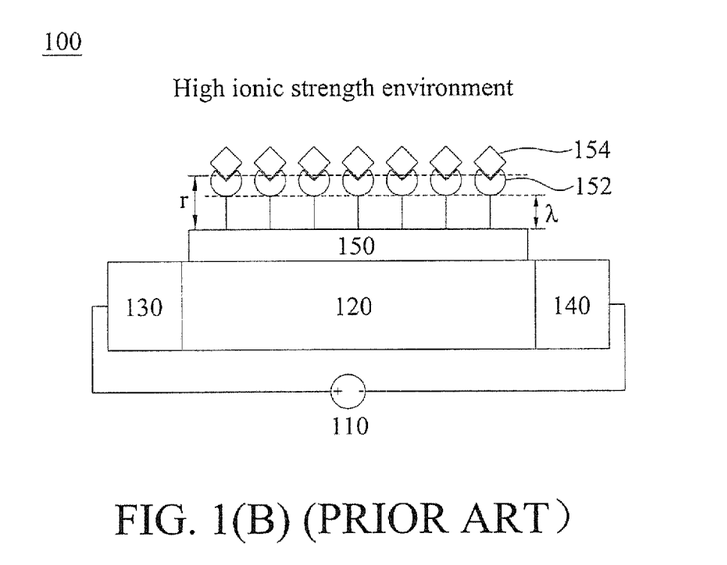

Various approaches for such detection have been reported in the literatures. For example, regarding the sample in high-ion fluid as shown in FIG. 1(B), some methods are performed by diluting the test sample to obtain low ionic strength condition to extend Debye length. However, in this manner, the measurement condition is substantially limited and cannot be employed in practical applications, such as a limitation due to a further dilution of a low concentration of target biomarkers. In another approach, to remove the ions in the test sample, the test sample must be pretreated with multiple and complicated processes which consume more time and cost. An electrochemical (EC) system can serve as a solution to resolve the issue of Debye length by providing EC signal for detection. However, a conventional EC system shows poor sensitivity when the concentration of target is low.

Hence, there is a need in the industry to overcome these problems of the conventional techniques.

SUMMARY OF THE DISCLOSURE

The present disclosure provides an electrochemical extended gate FET-based system, also referring as an electrochemical extended-gate transistor (EET) system, which is capable of avoiding Debye length issue and can be used directly to detect a target (for example, a biomarker) in high-ion fluid. Furthermore, an electrochemical method is applied in the EET system of the present disclosure, such that the concentration of a target can be determined by detecting the electrochemical signals generated by the redox in an ion fluid.

According the present disclosure, the EET system for detecting a target is provided, the EET system comprises: a field effect transistor (FET), having a gate, a source, and a drain; a potentiostat, having a working electrode, a counter electrode, and a reference electrode; wherein the working electrode is coupled with a detection region, and the counter electrode is coupled with the gate; wherein the detection region, the gate, and the reference electrode are arranged in an ion fluid; wherein the potentiostat is configured to generate redox in the ion fluid by an electrochemical method to detect the target.

In an embodiment, the FET comprises a readout unit coupled thereto for quantifying signals.

In an embodiment, the FET may be a n-MOS, a p-MOS FET, or any component with similar function.

In an embodiment, the substances in forming the working electrode, counter electrode, and reference electrode comprise at least one substance selected from the group consisting of gold, silver, platinum, palladium, carbon, indium tin oxide (ITO) glass, any conductive inks, and any combination thereof.

In an embodiment, the ion fluid may be in gas phase or liquid phase.

TABLE 1

Dimensions of Debye Length in Different Ionic Strength Environments

| Sample solutions | Ionic strength (mM) | Debye length (nm) | Reference |
|---|---|---|---|
| Blood | ~150 | ~0.7 | CN 85104506 B |
| Serum | ~150 | ~0.7 | Biosensors and Bioelectronics 2010, 25: 1767-1773 |
| Urine | — | 0.7~2.2 | Nano Lett. 2012, 12: 5245-5254 |
| 100 mM PBS pH 7.4 | ~400 | ~0.48 | Biomed Microdevices 2011, 13: 345-352 |
| 0.1 mM PBS pH 7.4 | ~0.4 | ~15.2 | Biomed Microdevices 2011, 13: 345-352 |

In an embodiment, the ion fluid may be an electrolyte, such as PBS, blood, serum, urine, saliva, sweat, or any solution having an ionic strength similar to physiological environment.

In an embodiment, the target comprises at least one selected from a group consisting of small molecule, protein, enzyme, antigen, antibody, nucleic acid, DNA, RNA, miRNA, aptamer, glycolipid, ligand, exosome or any biomarker for sensing applications.

In an embodiment, the detection region is modified with recognition elements having affinity or specificity to the target.

In an embodiment, the recognition elements can be any molecule having affinity or specificity to the target.

In an embodiment, the target may involve electrochemical (EC) activity.

Moreover, the present disclosure further provides a method for detecting a target, comprising: providing a FET having a gate, a source, and a drain; providing a potentiostat including a working electrode, a counter electrode, and a reference electrode, wherein the working electrode is coupled with a detection region, wherein the counter electrode is coupled with the gate, wherein the detection region, the gate, and the reference electrode are arranged in an ion fluid; and performing an electrochemical method driven by the potentiostat to generate redox in the ion fluid to detect the target.

In the present disclosure, the electrochemical method includes: voltammetry method, amperometry method, conductimetric method, impedance method, or any conventional electrochemical method.

| Reference Sign List | |
|---|---|
| 100 | Ordinary FET-based biosensor |
| 110 | Voltage source |
| 120 | Substrate |
| 130 | Drain |
| 140 | Source |
| 150 | Gate |
| 152 | Recognition element |
| 154 | Biomarker |
| 300 | EET system |
| 302 | Ion fluid |
| 310 | FET |
| 312 | Gate |
| 314 | Drain |
| 316 | Source |
| 320 | Detection region |
| 324 | Target |
| 330 | Potentiostat |
| 332 | Working electrode |
| 334 | Counter electrode |
| 336 | Reference electrode |
| 340 | Readout unit |
| 400 | EET system |
| 402 | Ion fluid |
| 404 | Mediator |
| 410 | FET |
| 412 | Gate |
| 414 | Drain |
| 416 | Source |
| 420 | Detection region |
| 422 | Recognition element |
| 424 | Target |
| 430 | Potentiostat |
| 432 | Working electrode |
| 434 | Counter electrode |
| 436 | Reference electrode |
| 440 | Readout unit |

DETAILED DESCRIPTION OF THE DISCLOSURE

The following specific embodiments are provided to illustrate the disclosure of the present disclosure, the advantages and effects can be apparently understood by those skilled in the art after reading the disclosure of this specification.

It should be understood, The accompanying drawings depicted structure, proportion, size, etc., are disclosed only to match the content of the specification, to facilitate the understanding and reading of those skilled in the art, but not intend to limit the present disclosure in specific conditions, and do not have technical substantial meaning. Any modification of the structure, change of the ratio relation, or adjustment of the size should be involved in the scope of disclosures in this specification without influencing the producible efficacy and the achievable objective of this specification. Those changes or adjustments of relative relationship without substantial change of technical content should also be considered within the category of implementation.

Figure 3:
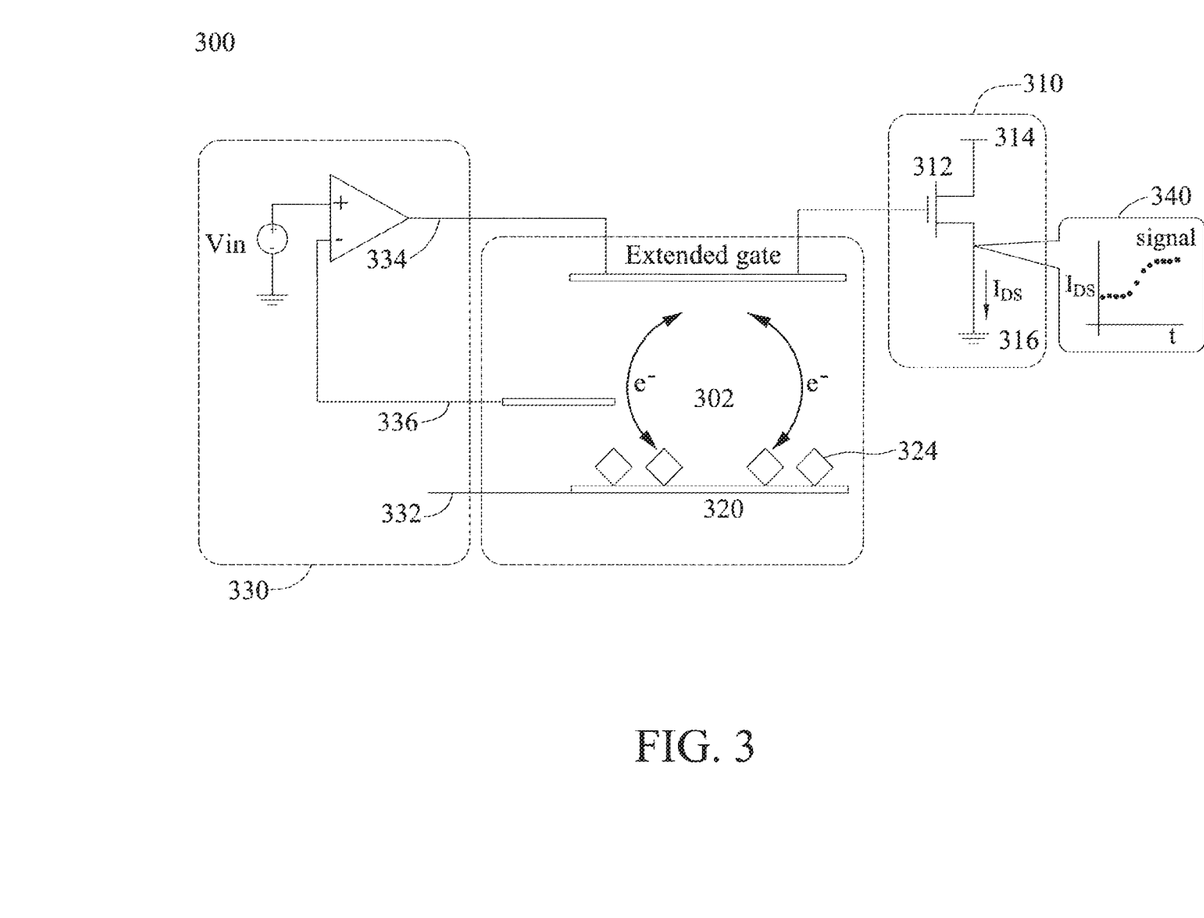
FIG. 3 shows a schematic view of the EET system according to an embodiment of the present disclosure, wherein the arrows show an exemplary direction for illustrating the direction of redox reaction.

FIG. 3 shows a schematic view of the EET system according to an embodiment of the present disclosure. The system 300 includes: a field effect transistor (FET) 310, having a gate 312, a source 316, and a drain 314; a potentiostat 330, having a working electrode 332, a counter electrode 334, and a reference electrode 336; wherein the working electrode 332 is coupled with a detection region 320, and the counter electrode 334 is coupled with the gate 312; wherein the detection region 320, the gate 312, and the reference electrode 336 are arranged in an ion fluid 302; wherein the potentiostat 330 is configured to generate redox in the ion fluid 302 to redox by an electrochemical method to detect the target 324.

The detection mechanism of the EET system according to an embodiment of the present disclosure is described in FIG. 3. For detecting the targets, the EET system 300 may include an electrochemical (EC) method, and the voltage difference between the working electrode 332 and counter electrode 334 will drive the target 324 in the ion fluid 302 to redox. In this way, the gate voltage of the FET 310 will thereby be controlled by the voltage of counter electrode 334 to induce a drain-to-source current ($I_{DS}$), which can be detected by the readout unit 340. Therefore, the concentration of the target 324 is presented as a function of the $I_{DS}$ detected by readout unit 340. Furthermore, some targets 324 may have specific electrochemical characteristic, such that when the potentiostat 330 performs an appropriate electrochemical method, the target 324 can generate corresponding faradic current and present a pair of redox peaks at a specific potential. Preferably, the detection region 320 of the EET system 300 may be modified with recognition elements (not shown in FIG. 3) having specificity to the target 324. When more recognition elements are combined with the target 324, the characteristic signal of the target 324 (e.g. peak current at redox potential) will also be measured. Besides, the signal may be further amplified by the FET 310, and the concentration of the target 324 can thereby be calculated and obtained by the readout unit 340 coupled with the FET 310.

Figure 4:
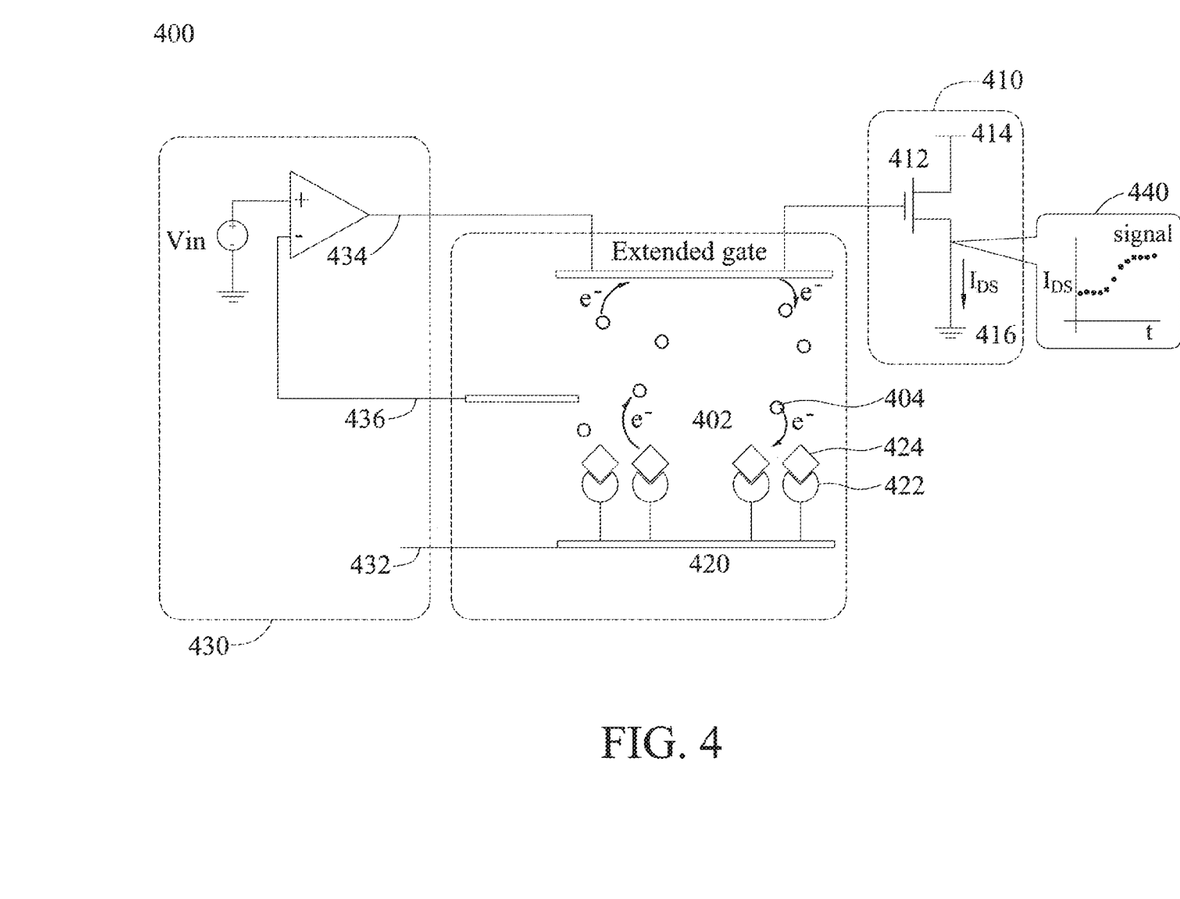
FIG. 4 shows a schematic view of the EET system according to an embodiment of the present disclosure, wherein recognition elements and mediators are introduced to the EET system.

FIG. 4 shows the EET system 400 according to another embodiment of the present disclosure. In the following, like numbers refer to like elements throughout this embodiment and the explanations that duplicate one another will be omitted. In this embodiment, the detection region 420 of the EET system 400 is modified with recognition elements 422 having specificity to the targets 424, and the targets 424 do not have electrochemical activity. Because the target 424 cannot generate enough redox current for target detection, in this embodiment, additional mediators 404 are added into the ion fluid 402 to facilitate the generation of the redox current. The mediator 404 can be any kind of mediator commonly used in this technical field, such as but not limited to, potassium ferricyanide, ferrocene, and tetrathiafulvalene (TTF). When an EC method is applied, the added mediators 404 are driven to generate redox current. In this way, when more recognition elements 422 are combined with targets 424, the resistance of the detection region 420 will change, and the redox current contributed by the mediator 404 will change correspondingly. Therefore, the concentration of the target 424 can be calculated by the readout unit 440 in this manner.

According to an embodiment of the present disclosure, a method for detecting a target 324 with the EET system 300 is provided and illustrated in FIG. 3. The method comprises: providing a field effect transistor (FET) 310 having a gate 312, a source 316, and a drain 314; providing a potentiostat 330 having a working electrode 332, a counter electrode 334, and a reference electrode 336; wherein the working electrode 332 is coupled with a detection region 320, wherein the counter electrode 334 is coupled with the gate 312, wherein the detection region 320, the gate 312, and the reference electrode 336 are arranged in an ion fluid 302; and performing an electrochemical method driven by the potentiostat 330 to generate redox in the ion fluid 302 to detect the target 324.

The present disclosure describes details with exemplarily embodiments. The present disclosure, however, should not be construed as being limited to the embodiments set forth herein.

Embodiment 1

The following experiment was carried out to illustrate that the EET system provided superior sensing performance (such as the limitation of the detection and the magnitude of the responses) even in physiological ionic strength environment. In this embodiment, the target was hemoglobin. The potentiostat was CHI6192E (CHI, Austin, Tex., USA), but other conventional potentiostat or equivalents could be used, and the working electrode, the counter electrode, and the reference electrode were respectively electrically coupled to a carbon electrode, a carbon electrode, and an Ag/AgCl electrode. Any appropriate pretreatment can be applied to the electrodes in the embodiment, such as cleaning by oxygen plasma, ethanol or deionized water. In addition, a person having ordinary skill in the art should understand that PBS is commonly used for simulating physiological environment in the technical field. The ion fluid was 100 mM PBS, prepared in 100 mM $Na_2HPO_4$ and 100 mM $NaH_2PO_4$, and the pH value was 7.4.

Afterwards, the EET system was used to measure the concentrations of hemoglobin solutions from 0.01 μg/ml to 100 μg/ml. During this measurement, an amperometry method was applied, and the voltage difference between the working electrode and the reference electrode was set at −0.4 V to drive corresponding redox reaction.

By comparison, a conventional EGFET system was used to detect hemoglobin. The configuration of the EGFET system and the detection condition were the same as those of the EET system mentioned above. A source-measurement unit was also utilized in the EGFET system but it merely was used for applying a potential with respect to the reference electrode and measuring signal.

The result of the measurement detected by a conventional EGFET system and the EET system of the present disclosure is shown in FIG. 5. In FIGS. 5(A) and 5(C), the x-axis refers to the measurement time, while in FIGS. 5(B) and 5(D), the x-axis refers to the concentration of hemoglobin. The y-axis refers to current ratio, $\Delta I_{DS}$ (change of the drain-to-source current)/$I_0$ (current detected in PBS without hemoglobin). The current ratio ($\Delta I_{DS}/I_0$) shown in y-axis is used for illustrating the normalized result of the detection, such that a person having ordinary skill in the art should easily understand the advantage and efficacy brought out by the present disclosure.

Figure 5A:
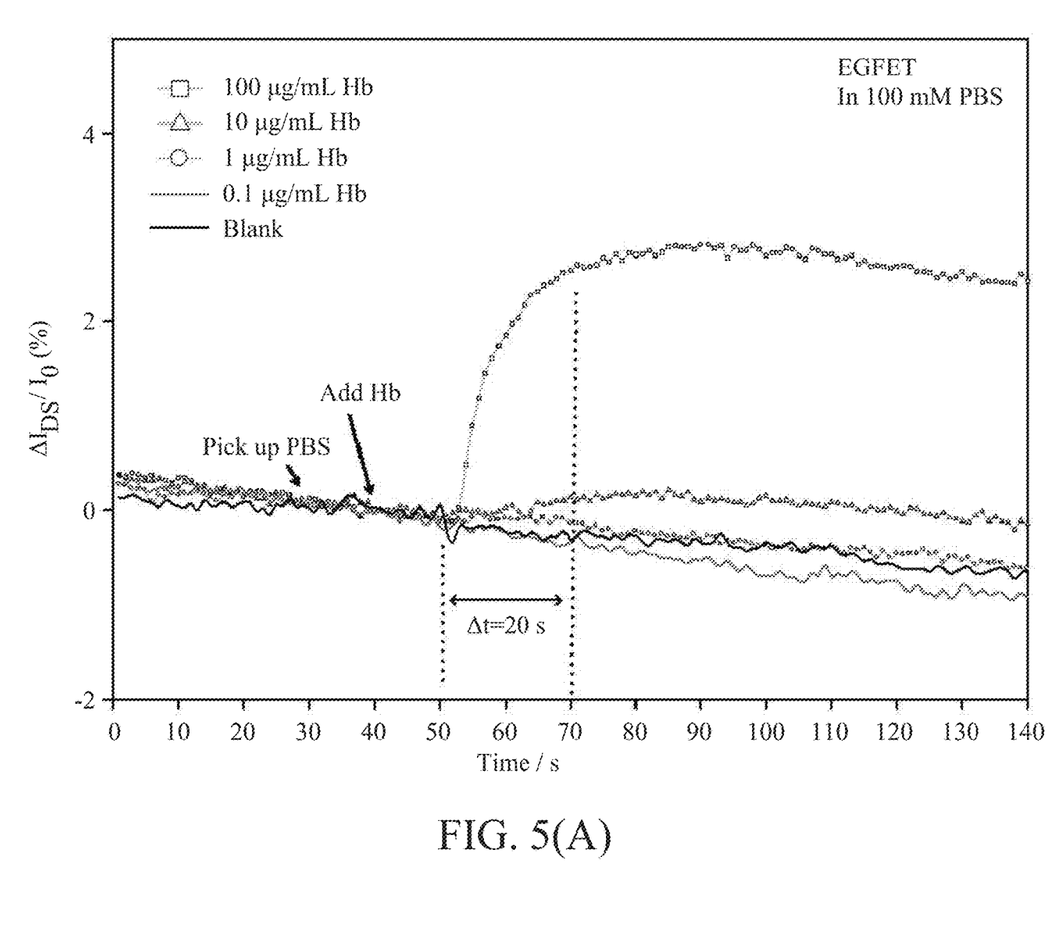
FIG. 5(A) shows a plot of time against the normalized current ratio detected by a conventional EGFET system according to an embodiment of the present disclosure for detecting hemoglobin.
Figure 5B:
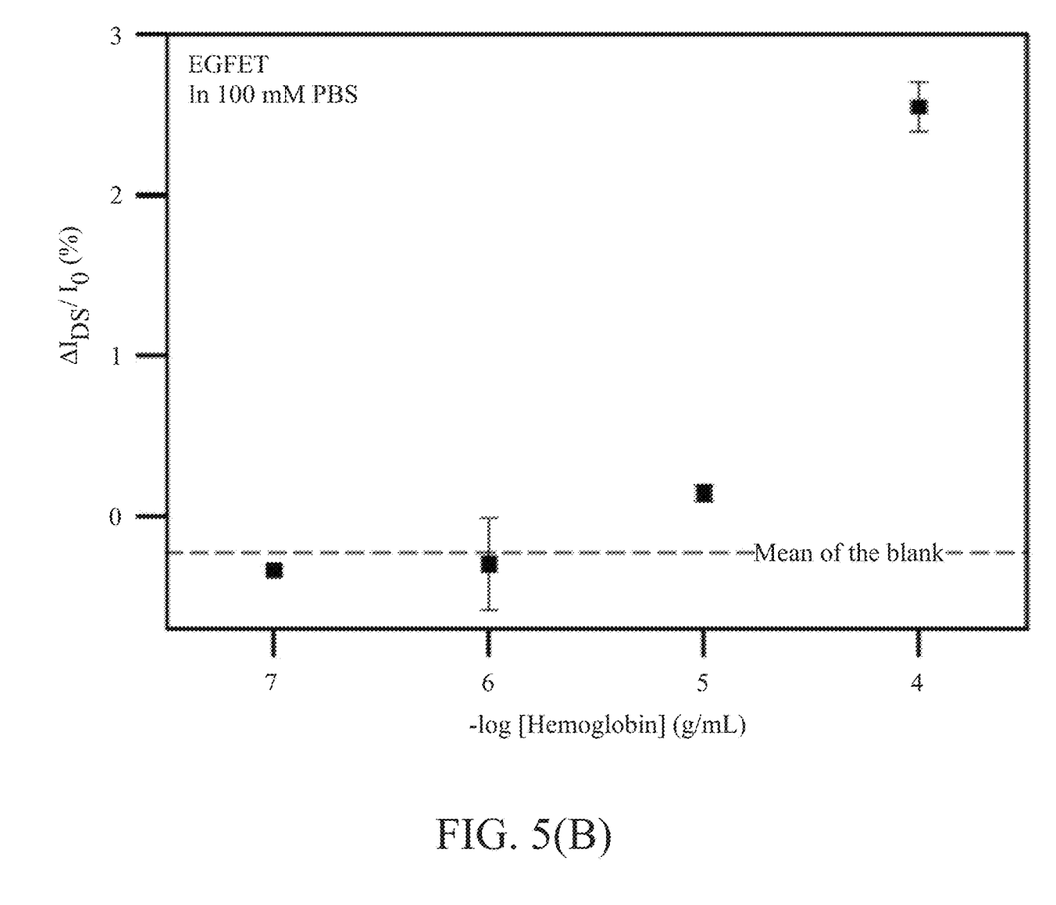
FIG. 5(B) shows a plot of concentration of hemoglobin against the normalized current ratio detected by a conventional EGFET system according to an embodiment of the present disclosure for detecting hemoglobin.

FIGS. 5(A) and 5(B) clearly show when the concentration of hemoglobin was equal or lower than 1 μg/ml, the signals measured by EGFET system was unobservable. Also, the detected signal (reference to current ratio) in 100 μg/ml of hemoglobin by the conventional EGFET system was merely 2%-3% higher than that of the blank (without hemoglobin).

Figure 5C:
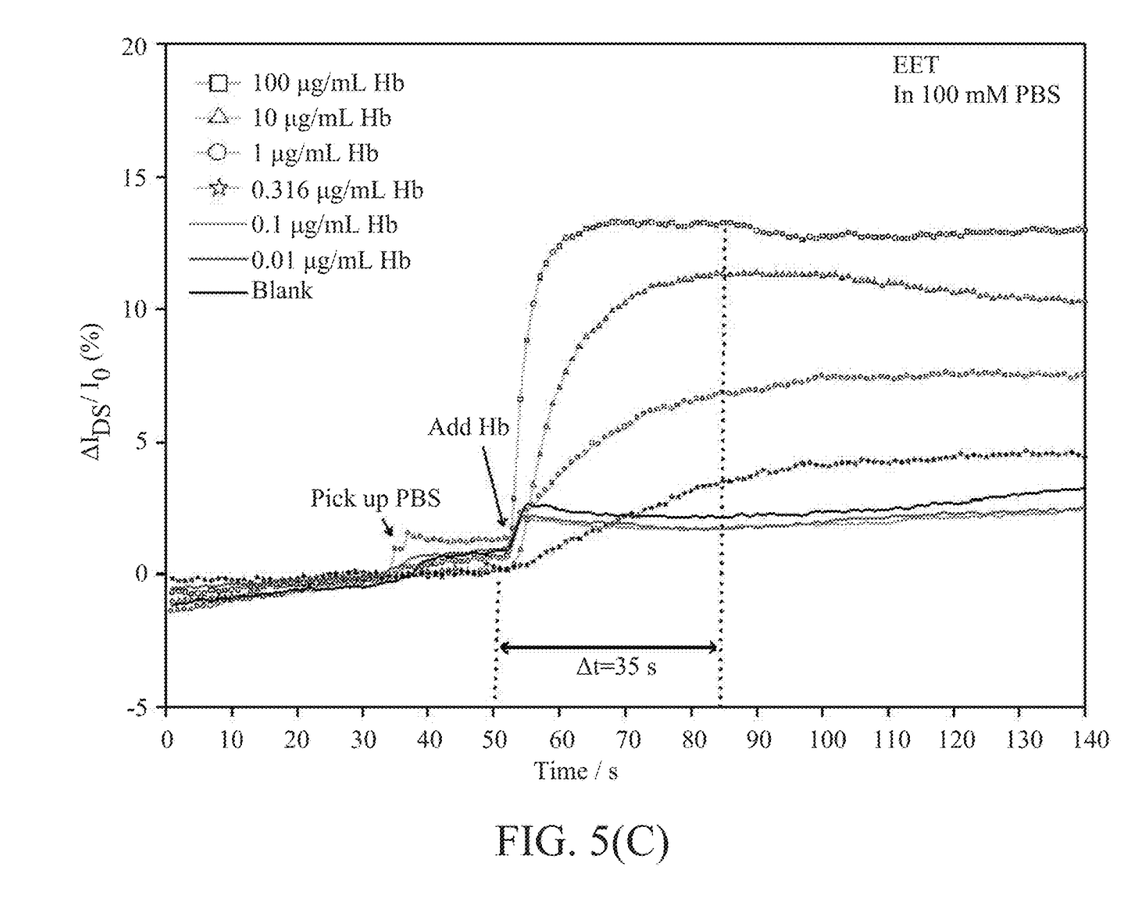
FIG. 5(C) shows a plot of time against the normalized current ratio detected by the EET system according to an embodiment of the present disclosure for detecting hemoglobin.
Figure 5D:
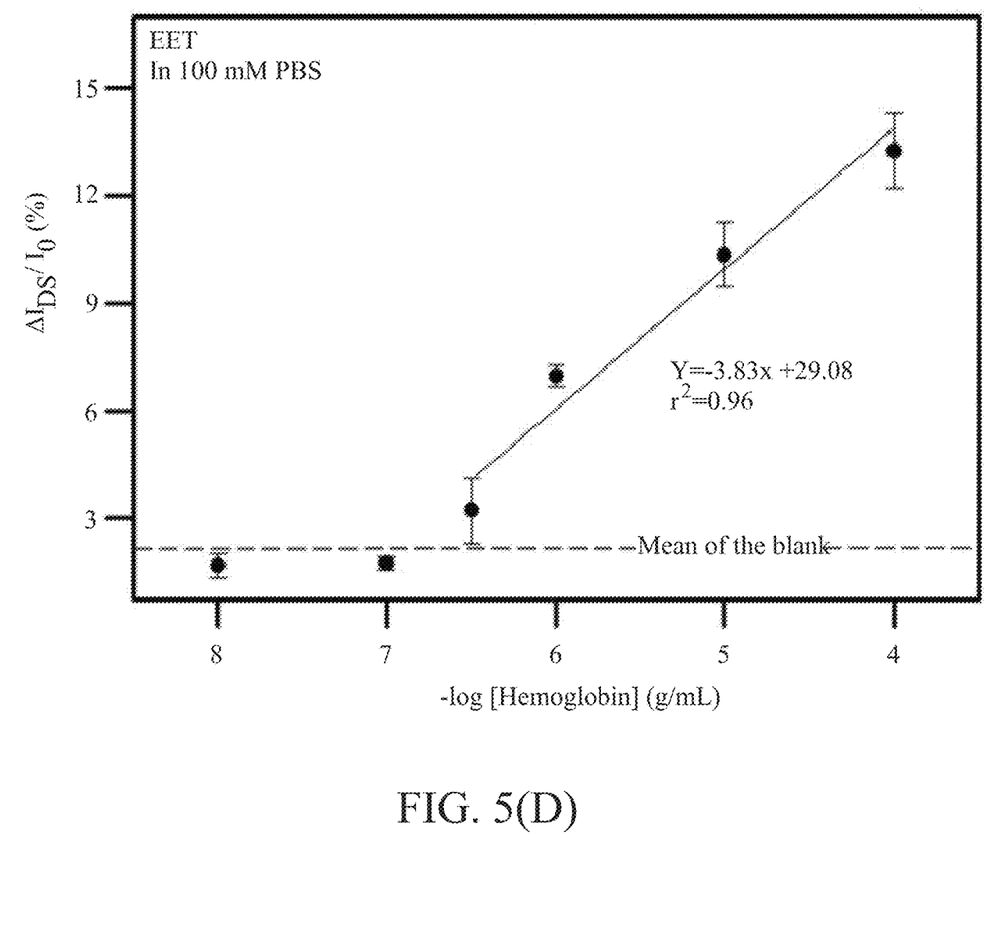
FIG. 5(D) shows a plot of concentration of hemoglobin against the normalized current ratio detected by the EET system according to an embodiment of the present disclosure for detecting hemoglobin.

In contrast, according to FIGS. 5(C) and 5(D), it shows a concentration-dependent correlation between the current ratio and concentration of hemoglobin. Also, the detection limit of the EET system was at least 30 times greater than that of the EGFET system and the detection range extended from 100 μg/ml to ~0.3 μg/ml of hemoglobin. Furthermore, the detected signal (reference to current ratio) increased ~3% with outstanding linearity, when the concentration of hemoglobin increased 10 times.

Embodiment 2

The experiment was carried out to illustrate that the EET system provided superior sensing performance comparing to a conventional EC system. In this embodiment, the sensing target was $H_2O_2$. A commercial strip (DEP-ER-P, BioDevice, Japan) was used in the embodiment, wherein the working, counter, and reference electrodes of the strip were of gold, carbon, and Ag/AgCl, respectively. The potentiostat was CHI6192E (CHI, Austin, Tex., USA). The ion fluid in this embodiment was PBS (100 mM $Na_2HPO_4$ and 100 mM $NaH_2PO_4$; pH 7.4). Before the measurement, the electrode strip was cleaned by ethanol and deionized water and further dried by nitrogen gas.

Afterwards, the EET system was used to measure the concentrations of $H_2O_2$ solutions from 1 nM $H_2O_2$ to 100 μM $H_2O_2$. During this measurement, the amperometry method was applied, and the voltage difference between the working electrode and the reference electrode was set at 0.25 V to drive corresponding redox reaction. The detection environment of the EC system was similar to that of the EET system mentioned above.

The results of the measurement obtained by using a conventional EC system and the EET system of the present disclosure are shown in FIG. 6. In FIGS. 6(A) and 6(B), $\Delta I_{CW}$ represents change of the counter-to-working current. The results show that the detected signals were undistinguishable when the concentration of $H_2O_2$ was equal or lower than 1 μM. To be more specific, the detection limit was 10 μM.

Figure 6A:
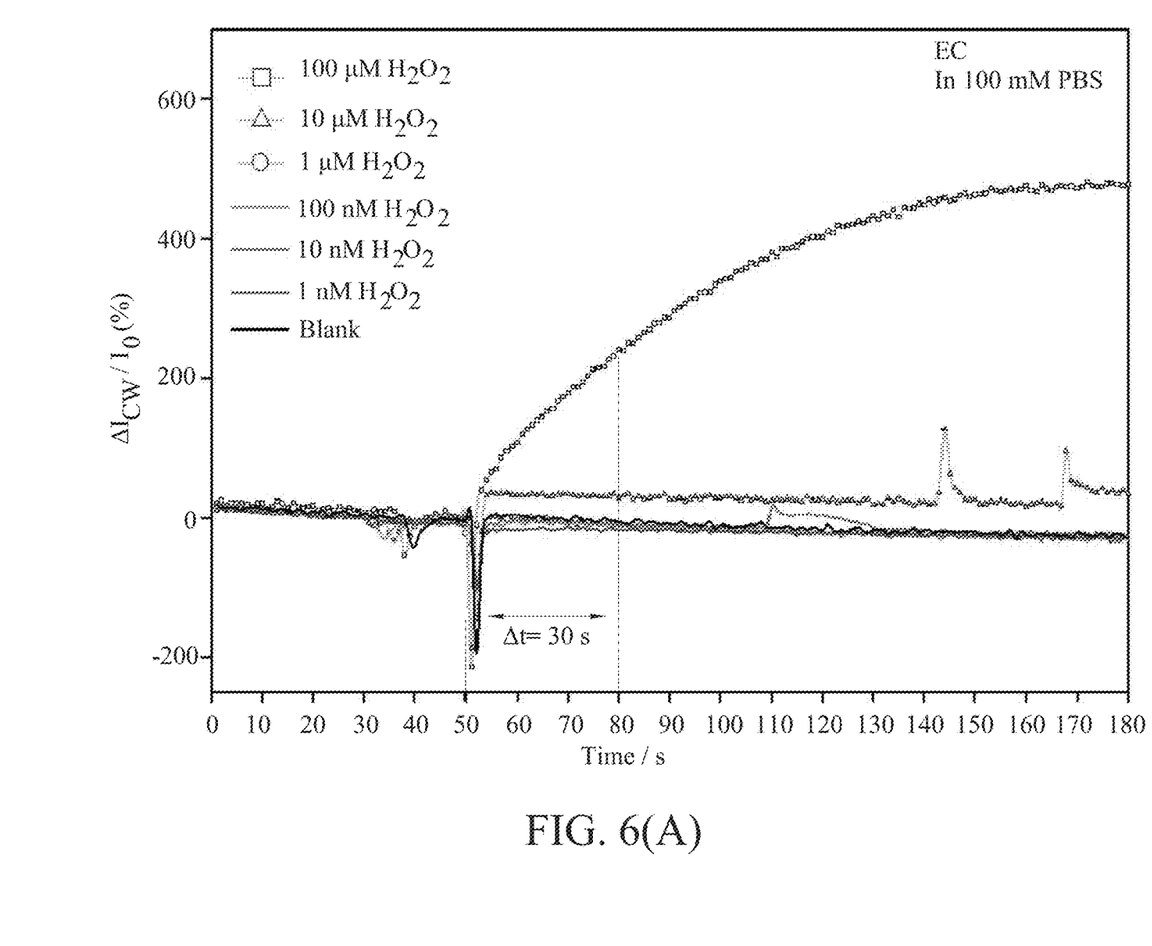
FIG. 6(A) shows a plot of time against the normalized current ratio detected by a conventional EC system according to an embodiment of the present disclosure for detecting $H_2O_2$.
Figure 6B:
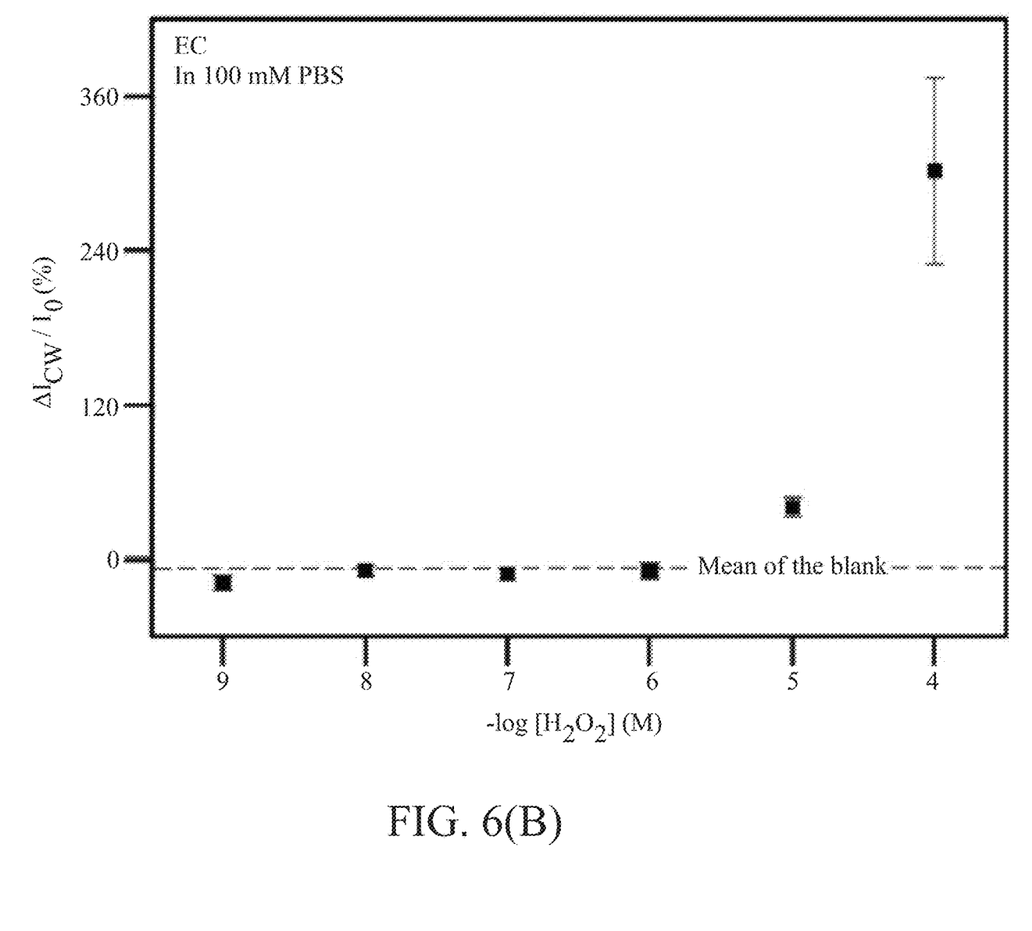
FIG. 6(B) shows a plot of concentration of $H_2O_2$ against the normalized current ratio detected by a conventional EC system according to an embodiment of the present disclosure for detecting $H_2O_2$.
Figure 6C:
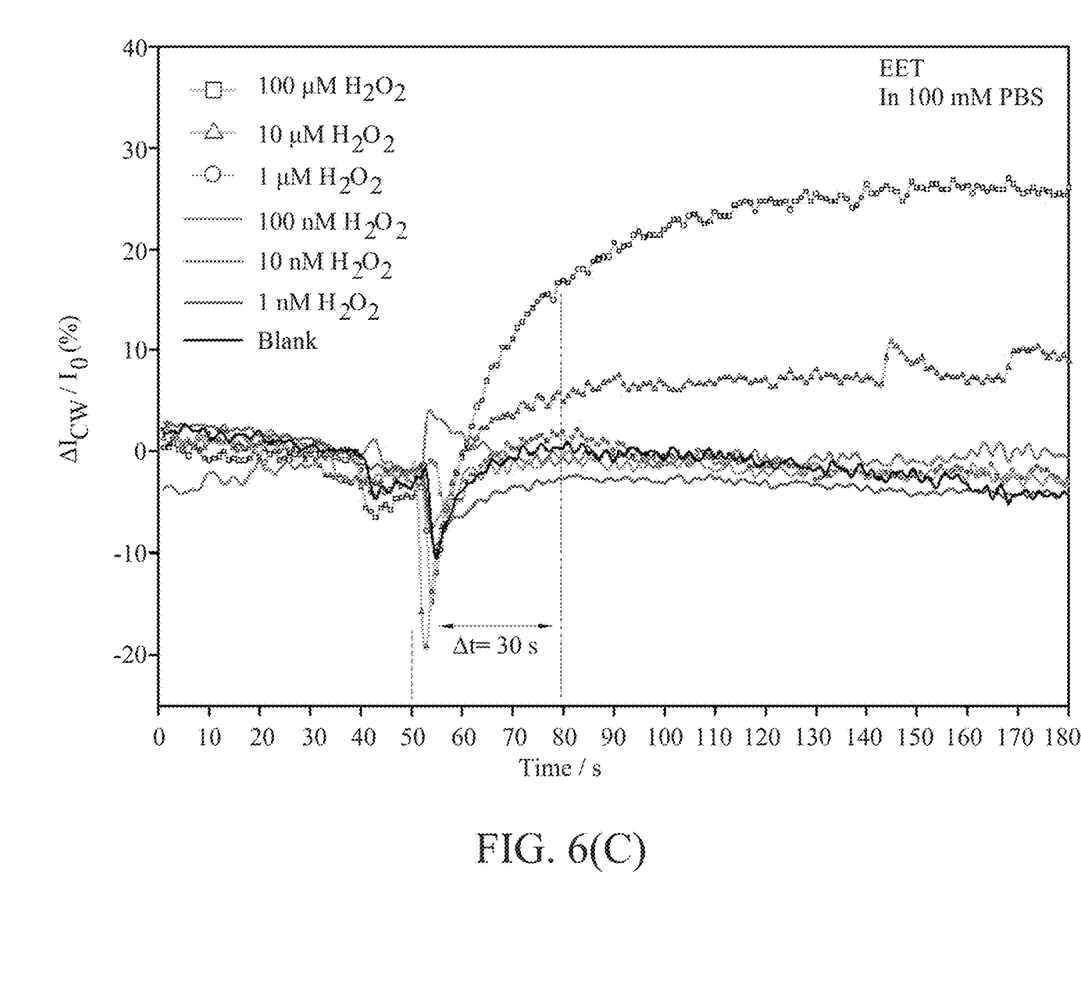
FIG. 6(C) shows a plot of time against the normalized current ratio detected by the EET system according to an embodiment of the present disclosure for detecting $H_2O_2$.
Figure 6D:
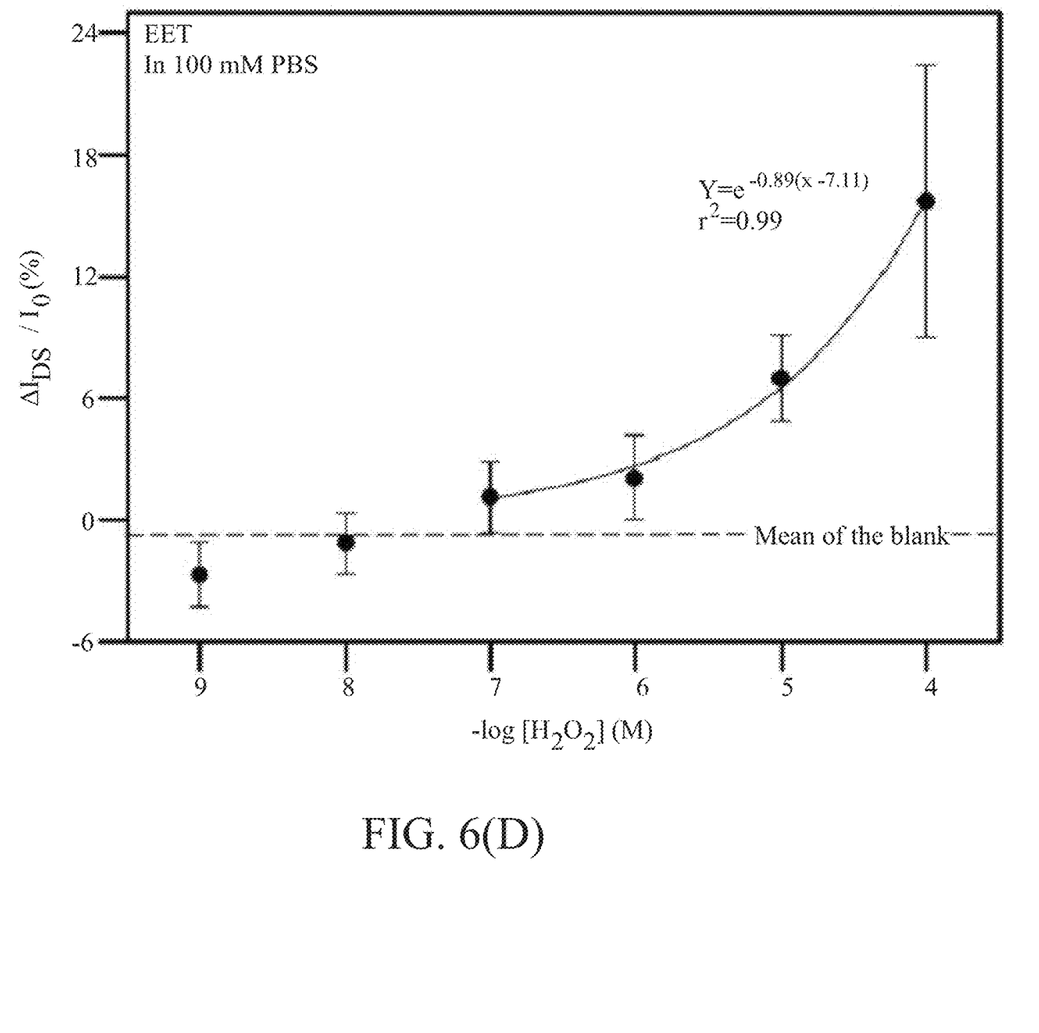
FIG. 6(D) shows a plot of concentration of $H_2O_2$ against the normalized current ratio detected by the EET system according to an embodiment of the present disclosure for detecting $H_2O_2$.

In contrast, according to FIGS. 6(C) and 6(D), the results show a concentration dependent correlation between the current ratio and concentration of $H_2O_2$. Also, the detection limit of the EET system was at least 100 times greater than that of the EC system and the detection range extended from 100 μM to 0.1 μM of $H_2O_2$.

Figure 7:
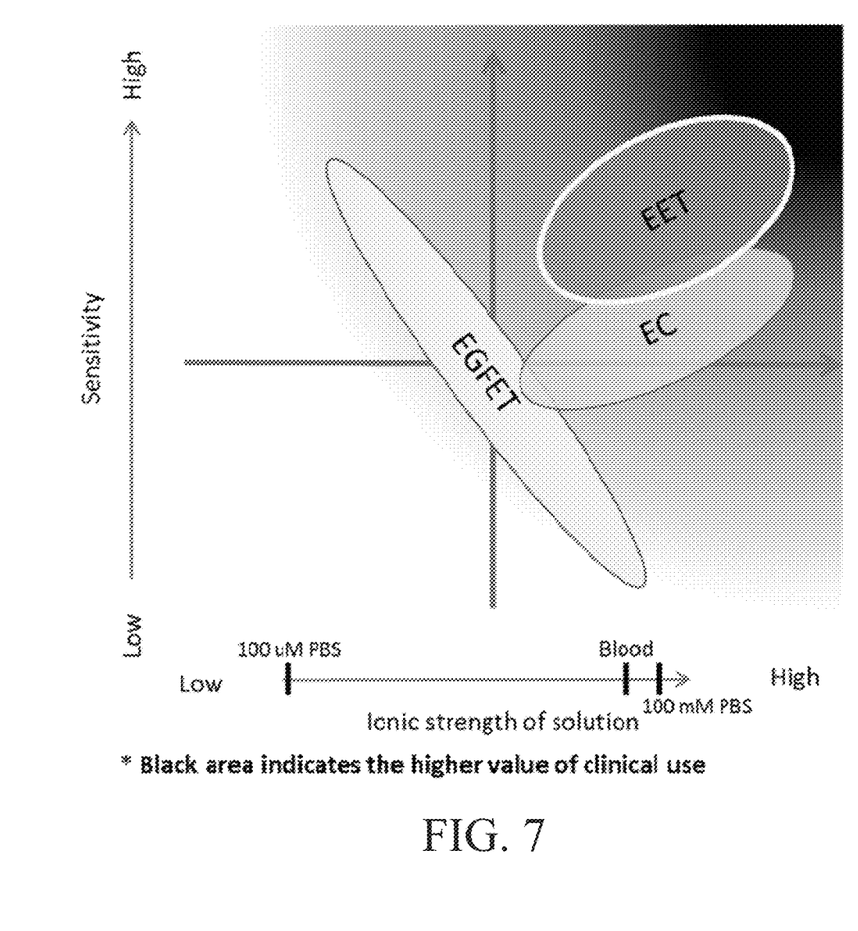
FIG. 7 shows a plot for comparing the industrial value of the EET system of the present disclosure with the conventional EGFET and EC systems.

From the foregoing, the description and the embodiments clearly illustrate the advantage and efficacy brought out by the EET system of the present disclosure. More specifically, the EET system of the present disclosure can further amplify the detected signal utilizing the FET configuration within the EET system. As shown in Table 2, the present disclosure demonstrates that the EET system of the present disclosure can not only improve EGFET's limit of Debye length in a high-ion fluid, but also increase EC measurement's sensitivity in a lower concentration scenario. In addition, with the utilization of mediator, the EET system of the present disclosure can measure the concentration of the target no matter it has electrochemical activity or not, such that more flexibility for detection is provided. In summary, the present disclosure successfully provides a EET detection system which provides outstanding sensitivity and performs well in a high-ion fluid. As shown in FIG. 7, the EET system of the present disclosure has higher value in sensing applications comparing to the EGFET and EC systems.

TABLE 2

A Summary of Detection Limits of the EET System and Present Disclosure

|  | EC | EGFET | EET | Conclusion |
| --- | --- | --- | --- | --- |
| Hemoglobin (In 100 mM PBS, pH 7.4) | — | ~10 μg/ml | ~0.3 μg/ml | (EET vs. EGFET) Improve the limit of debye length ~30-fold |
| $H_2O_2$ (In 100 mM PBS, pH 7.4) | ~10 μM | — | ~0.1 μM | (EET vs. EC) Increase sensitivity ~100-fold |

The present disclosure has been described using exemplary embodiments to illustrate the principles and the effects of the present disclosure, but not intend to limit the present disclosure. The present disclosure without departing from the spirit and scope of the premise can make various changes and modifications by persons skilled in the art. Therefore, the scope of protection of the rights of the disclosure, the claims should be listed in the book. Therefore, the scope of the disclosure should be defined by the appended claims.

What is claimed is:

1. A system for detecting a target in an ion fluid, comprising:
    a field effect transistor (FET), having a gate, a source, and a drain, wherein the FET is an extended gate FET;
    a potentiostat, having a working electrode, a counter electrode, and a reference electrode;
    wherein the working electrode is coupled with a detection region and without being directly coupled with the gate and with being coupled with an extended gate by the ion fluid;
    wherein the extended gate is wired directly to the gate of the FET, and the extended gate functions as the counter electrode;
    wherein the detection region, the extended gate, and the reference electrode are arranged in the ion fluid;
    wherein the potentiostat is configured to generate redox in the ion fluid by an electrochemical method to detect the target;
    wherein a gate voltage of the FET is controlled by the voltage of counter electrode to induce a drain-to-source current ($I_{DS}$), and the concentration of the target is presented as a function of the $I_{DS}$ detected by a readout unit;

wherein the readout unit is directly wired to the source of the FET.

2. The system of claim 1, wherein the FET comprises the readout unit coupled thereto for quantifying signals.

3. The system of claim 1, wherein the target has an electrochemical activity.

4. The system of claim 1, wherein the target comprises at least one selected from a group consisting of small molecule, protein, nucleic acid, and glycolipid, and any combination thereof.

5. The system of claim 1, wherein the ion fluid is in liquid phase.

6. The system of claim 5, wherein the liquid phase of the ion fluid is an electrolyte.

7. The system of claim 1, wherein the ion fluid comprises a mediator.

8. The system of claim 1, wherein the detection region is modified with recognition elements having affinity or specificity to the target.

9. A method for detecting a target in an ion fluid, comprising:
providing a field effect transistor (FET) having a gate, a source, and a drain, wherein the FET is an extended gate FET;
providing a potentiostat having a working electrode, a counter electrode, and a reference electrode, wherein the working electrode is coupled with a detection region and without being directly coupled with the gate and with being coupled with an extended gate by the ion fluid;
wherein the extended gate is wired directly to the gate of the FET, and the extended gate functions as the counter electrode;
arranging the detection region, the extended gate, and the reference electrode in the ion fluid;
performing an electrochemical method driven by the potentiostat to generate redox in the ion fluid to detect the target;
wherein a gate voltage of the FET is controlled by the voltage of counter electrode to induce a drain-to-source current ($I_{DS}$), and the concentration of the target is presented as a function of the $I_{DS}$ detected by a readout unit;
wherein the readout unit is directly wired to the source of the FET.

10. The method of claim 9, further comprising quantifying signals produced by the redox of the target by the readout unit coupled to the FET.

11. The method of claim 9, wherein the target has an electrochemical activity.

12. The method of claim 9, wherein the target comprises at least one selected from a group consisting of small molecule, protein, nucleic acid, and glycolipid, and any combination thereof.

13. The method of claim 9, wherein the ion fluid is in liquid phase.

14. The method of claim 13, wherein the liquid phase of the ion fluid is an electrolyte.

15. The method of claim 9, wherein the ion fluid further comprises a mediator.

16. The method of claim 9, wherein the detection region is modified with recognition elements having affinity or specificity to the target.

17. The method of claim 9, wherein the electrochemical method is at least one selected from the group consisting of a voltammetry method, an amperometry method, and any combination thereof.

* * * * *